(12) United States Patent
Vanderspurt et al.

(10) Patent No.: US 8,946,494 B2
(45) Date of Patent: Feb. 3, 2015

(54) METHOD FOR PROCESSING BIOMASS

(75) Inventors: Thomas Henry Vanderspurt, Brick, NJ (US); Timothy D. Davis, Portland, OR (US); Sean C. Emerson, Broad Brook, CT (US); Ying She, East Hartford, CT (US); Rhonda R. Willigan, Manchester, CT (US); Salvatore Saitta, Willington, CT (US); Tianli Zhu, Cheshire, CT (US)

(73) Assignee: United Technologies Corporation, Hartford, CT (US)

( * ) Notice: Subject to any disclaimer, the term of this patent is extended or adjusted under 35 U.S.C. 154(b) by 759 days.

(21) Appl. No.: 13/224,533

(22) Filed: Sep. 2, 2011

(65) Prior Publication Data
US 2013/0055627 A1  Mar. 7, 2013

(51) Int. Cl.
C07C 1/00 (2006.01)
C10L 1/02 (2006.01)

(52) U.S. Cl.
CPC .............. *C10L 1/026* (2013.01); *C07C 2101/14* (2013.01); *C10G 2300/1014* (2013.01); *C10G 2300/42* (2013.01); *Y02E 50/13* (2013.01)
USPC .............................. 585/240; 201/21; 585/242

(58) Field of Classification Search
USPC ............... 585/240, 242; 44/606; 162/22, 173; 201/21
See application file for complete search history.

(56) References Cited

U.S. PATENT DOCUMENTS

| | | | |
|---|---|---|---|
| 4,605,790 A | 8/1986 | Wojtkowski | |
| 5,959,167 A | 9/1999 | Shabtai et al. | |
| 6,043,392 A | 3/2000 | Holtzapple et al. | |
| 7,880,049 B2 | 2/2011 | Dumesic et al. | |
| 7,931,784 B2 * | 4/2011 | Medoff | 204/157.63 |
| 8,013,195 B2 * | 9/2011 | Mccall et al. | 585/240 |
| 2009/0239279 A1 | 9/2009 | Hall et al. | |
| 2010/0175320 A1 | 7/2010 | Schuetzle et al. | |
| 2010/0297749 A1 | 11/2010 | Aravanis et al. | |
| 2010/0317070 A1 * | 12/2010 | Agaskar | 435/126 |
| 2011/0008865 A1 | 1/2011 | Lee | |
| 2011/0272108 A1 * | 11/2011 | Prochazka et al. | 162/38 |
| 2011/0275868 A1 * | 11/2011 | Prochazka et al. | 585/242 |

OTHER PUBLICATIONS

Thring, "Alkaline Degradation of Alcell Lignin", Biomass and Bioenergy vol. 7, No. 1-6, pp. 125-130, 1994.
Chakar et al., "Review of Current and Future Softwood Kraft Lignin Process Chemistry", Industrial Crops and Products 20 (2004) pp. 131-141.
Benigni et al., "Neutral Hydrolysis of Alkali Lignin to Monomeric Phenols", J. Polymer Sco.: Part C, pp. 467-475, 1971.

* cited by examiner

*Primary Examiner* — Nina Bhat
(74) *Attorney, Agent, or Firm* — Carlson, Gaskey & Olds, P.C.

(57) ABSTRACT

A method for processing biomass to produce biofuel includes decomposing lignocellulosic material into byproduct polymers that include lignin, decomposing the lignin into targeted chemical fragments, and chemically converting the targeted chemical fragments into a biofuel.

18 Claims, 2 Drawing Sheets

METHOD FOR PROCESSING BIOMASS

STATEMENT REGARDING FEDERALLY SPONSORED RESEARCH OR DEVELOPMENT

This invention was made with government support under contract number SUB-226-UTC1 awarded by DARPA. The government has certain rights in the invention.

BACKGROUND

This disclosure relates to the chemical processing of biomass material to produce useful byproducts.

Biomass material is known and used as a renewable energy source. Among other uses, biomass material is chemically processed to produce useful byproducts, such as biofuels for energy production.

Lignocellulosic biomass material is a plant biomass that is composed of cellulose, hemicellulose and lignin. In a typical process to convert lignocellulosic biomass to useful byproducts, the lignocellulosic biomass material is broken down into its three main components. The cellulose component and hemicellulose component are further chemically processed to produce the useful byproducts. The lignin portion of the lignocellulosic biomass material is a complex chemical compound that is not used to produce the useful byproducts. The fermentation and processing methods that break down the cellulose and hemicellulose portions of the lignocellulosic biomass material are not effective to break down the lignin. The lignin is therefore an unusable waste byproduct.

DETAILED DESCRIPTION

Figure 1:
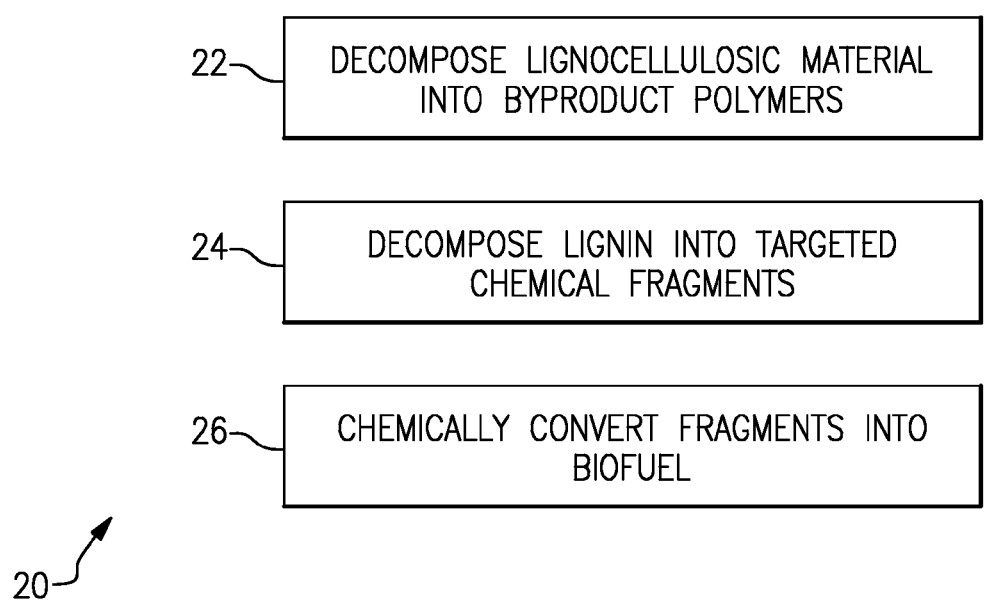
FIG. 1 illustrates an example method for processing a biomass material to produce a biofuel.

FIG. 1 schematically shows an example method 20 for processing biomass material to produce biofuel. As will be described, the feed stock biomass material for the exemplary method 20 is a lignocellulosic material. The disclosed method 20, unlike other methods of processing lignocellulosic materials, utilizes the lignin portion of the lignocellulosic biomass material to produce a useful byproduct, such as a biofuel. For instance, the biofuel is jet fuel.

In the illustrated example, the method 20 includes a first decomposition step 22, a second decomposition step 24 and a chemical conversion step 26. In general, the first decomposition step 22 involves the decomposition of a lignocellulosic material into byproduct polymers that include lignin. As is known, lignocellulosic material generally includes three primary constituents, cellulose, hemicellulose and lignin. In the method 20, the lignin portion of the lignocellulosic material is then further decomposed into targeted chemical fragments in the second decomposition step 24. In the chemical conversion step 26, the targeted chemical fragments of the lignin are chemically converted into a biofuel. In one example, the biofuel is a hydrocarbon having a number of carbon atoms in the range of jet fuel.

FIG. 1 illustrates the broad steps of the exemplary method 20. It is to be understood that additional steps may accompany the disclosed steps 22, 24 and 26 in a particular implementation of the method 20. The following working examples disclose additional embodiments of the method 20. Given this description, one of ordinary skill in the art will recognize how to modify the examples disclosed herein to meet their particular needs when processing lignocellulosic material to make use of the lignin portion.

In one example, the first decomposition step 22 involves decomposing the lignocellulosic material in a slurry having a pH level of 8 or greater at a temperature between 180° C. and 250° C. In a further example, the slurry is an aqueous slurry and includes an alkaline component to maintain the slurry at the desired pH level. In some examples, the alkaline component includes at least one of potassium carbonate, sodium carbonate, potassium hydroxide, sodium hydroxide, or wood ash extract.

In a further example, the lignocellulosic material in the slurry is decomposed in the presence of a heterogeneous catalyst and in an environment having a total gas pressure of greater than 5 atmospheres. This total gas pressure may be composed of hydrogen, nitrogen, carbon dioxide, or mixtures thereof. In a further example, the hydrogen pressure is approximately 10 atmospheres. As an example, the decomposition step 22 is conducted in a reactor vessel of suitable construction to achieve the desired conditions.

In a further example, the first decomposition step 22 also includes separating the lignin from the byproduct cellulose and hemicellulose polymers. For instance, the lignin portion of the lignocellulosic material is separated using a combination of cyclones, filters and chemical extraction.

After the separation of the lignin portion, the slurry is substantially free of lignin. The byproduct cellulose and hemicellulose polymers in the slurry are then catalytically reformed in the presence of a reforming catalyst to produce hydrogen and byproduct organic acids and unreacted solids. In an example, the catalytic reforming is conducted at a temperature of 300-330° C. with a ratio of base to wood (weight of base divided by weight of wood, g/g) of 0.2-1.0. In a further example, the ratio is 0.5-1.0. In one example, the hydrogen is fed back into the first decomposition step 22 and/or step 24 to facilitate the decomposition of the lignocellulosic material.

In one example, the second decomposition step 24 includes catalytically decomposing the lignin portion to produce targeted chemical fragments. The catalytic decomposing of the lignin is conducted using a catalyst that includes at least one of cobalt, nickel, tin, platinum, rhenium, palladium or combinations thereof, which are used either with or without a catalyst support material. In some examples, the targeted chemical fragments of the lignin include oxygenates. The oxygenates include, for example, simple alcohols, cyclic alcohols, and methoxy benzenes, and mixtures thereof. The cyclic alcohols include compounds such as cyclopentanols, cyclohexanols, alkylcyclopentanols, alkylcyclohexanols, phenols, alkylphenols, or mixtures thereof. In a further example, the fragments of the lignin are hydrocarbons having 9 or less carbon atoms. The second decomposition step 24 may be conducted in combination with or separately from the first decomposition step 22. That is, the second decomposition step 24 may be conducted prior to or after separation of the lignin from the byproduct cellulose and hemicellulose polymers.

In one example, the chemical conversion step 26 includes converting the targeted chemical fragments of the lignin to produce the biofuel. In one example, the conversion involves a coupling reaction and the resulting biofuel includes hydrocarbons having from 9 to 16 carbon atoms.

In a further example, the chemical conversion step 26 includes chemically converting the fragments of the lignin by reacting the fragments with each other to produce the biofuel.

In a further example, the resultant biofuel includes at least 9 carbon atoms and the targeted chemical fragments include 9 carbon atoms or less.

The following is a further example of the method 20 and process streams involved in the method. In this example, the lignocellulosic material is ground and formed into a pumpable slurry that is purged to be free of air. The slurry is then heated and agitated at a temperature from 180° C. to 250° C. In one example, the heating is conducted in stages to gradually achieve the target temperature. Once at temperature, or alternatively prior to reaching the targeted temperature, the pH of the slurry is increased to a pH level of 8 or greater. In a further example, the pH is increased to a level of 10 or greater.

The slurry is heated to the targeted temperature in an environment of at least 10 atmospheres pressure of hydrogen in the presence of a heterogeneous catalyst.

The catalyst is employed as a fixed bed catalyst or a free catalyst that is mixed with the slurry. If a fixed bed catalyst is used, the catalyst components may be separated into sequential catalytic beds, such that the catalytic material on each bed is targeted to achieve a different decomposition function, such as aromatic ring hydrogenation, carbon-oxygen bond hydrogenolysis or aldehyde reduction.

Under the given temperature and pressure conditions, the lignocellulosic material decomposes into the constituent cellulose, hemicellulose and lignin components. The conditions also function to decompose or depolymerize the lignin component by hydrogenation and hydrogenolysis. In one example, the hydrogenation and hydrogenolysis of the lignin portion of the lignocellulosic material results in the conversion of the lignin to cyclohexanols and phenols. These fragments can then later be extracted from the slurry and further processed to produce biofuel. The treatment of the slurry at the high temperature and under high hydrogen pressure also functions to solubilize the hemicellulose and non-crystalline cellulose portions of the lignocellulosic material.

The slurry is then further processed to separate the lignin portion from the other byproduct polymers and decomposition products. For example, the lignin is separated using a combination of cyclones, filters and chemical extractions. The separation results in a first process stream that includes the cellulose and hemicellulose portions and second process stream that includes the lignin fragments. The lignin fragments are then extracted from the second stream using a water immiscible organic solvent or super-critical carbon dioxide. For instance, the extraction removes hydrocarbon compounds having five carbon atoms or more, such as cyclohexanols and phenols.

The first stream that includes the cellulose and hemicellulose decomposition products is further processed by adjusting the pH to a level greater than 8. The resulting solution is then heated at a temperature from 280° C. to 330° C. over a reforming catalyst to produce hydrogen. In an example, the catalytic reforming is conducted at a temperature of 300-330° C. with a ratio of base to wood (weight of base divided by weight of wood, g/g) of 0.2-1.0. In a further example, the ratio is 0.5-1.0. A selective membrane or other separation device may used to separate the hydrogen in the reforming process. The hydrogen is fed back into the first decomposition step 22 and/or step 24 to facilitate the decomposition of the lignocellulosic material.

The decomposition of the lignocellulosic material also results in the production of a cellulosic fibril byproduct. The cellulosic fibrils are optionally washed in water to remove excess base solution. The wash water may then be fed back into the first decomposition step 22. The cellulose fibrils are then fed as an aqueous slurry for acid hydrogenolysis in the presence of one or more heterogeneous catalyst to convert the cellulose to a hydrocarbon material having 6 carbon atoms. This hydrocarbon material is then extracted from the aqueous solution for later use in the process. The remaining light compounds are fed back into the reforming process to produce hydrogen. The remaining solution from the reforming reaction is filtered or cycloned to remove the solids and unreacted organic matter. The organic matter is recovered and sent to a burner to produce useful heat. The remaining aqueous effluent after separation of the solids is fed back into the first decomposition step 22 to facilitate forming the slurry with the lignocellulosic material.

The fragments from the decomposition of the lignin and the hydrocarbon material having 6 carbon atoms produced from the cellulosic portion of the lignocellulosic material are fed into a reactor with hydrogen and in the presence of a catalyst, such as a supported metal/mixed metal oxide catalyst. The fragments are chemically converted into the biofuel. In one example, the biofuel includes 2-cyclohexyl-cyclohexanol and/or 2-phenylcyclohexanol, bi-cyclohexyl, bi-cyclohexyl-2-one, bi-cyclohexane. The resultant biofuel is optionally further processed to reduce oxygen content.

The following examples disclose additional embodiments of one or more of the first decomposition step 22 and the second decomposition step 24 of the method 20.

EXAMPLE 1-1

A 500 cc Inconel stirred autoclave was charged with 28 g wood flour, 250 g water, 14 g of KOH and 14 g Raney Ni catalyst. The reactor was sealed, flushed with nitrogen and pressurized with nitrogen to 100 psig and then hydrogen to total pressure 600 psig. The reactor was heated to 200° C. and maintained at temperature for 6 hr under stirring. After the mixture was cooled, the residual gas was analyzed. The product mixture was withdrawn, the reactor was rinsed with water and the wash was combined with the product mixture. This product mixture was filtered and the residue washed with water. An aliquot of the liquid was acidified with 2M $H_2SO_4$ to a pH of 1-2. The acidified liquor was extracted with ether three times and then with ethyl acetate three times. The resulting ether extract and ethyl acetate extract was then analyzed by gas chromatography with mass spectrometer (GCMS). 1-butanol was used as internal standard for the measurement and the yield of phenolics, cyclic alcohols, methoxybenzene were calculated on the basis of total lignin that can be converted to cyclic precursors. The effect of base concentration and temperature on hydrolysis are illustrated in examples 2-4.

EXAMPLES 2-1 to 4-1

The effect of temperature and base concentration on the product yield and distribution was studied in examples 2-1 to 4-1. The process described in example 1-1 was repeated except in example 2-1 the reaction temperature was increased to 250° C. In example 3-1, 84 g KOH was used and the reaction temperature was kept at 200° C. Example 4-1 used 7.5 g KOH while everything else is the same as in Example 3-1. The results are summarized in Table 1 below. In further examples, the temperature is 200-250° C. and a ratio of base (e.g. KOH) to wood (weight of base divided by weight of wood g/g) is controlled to be within a range of 0.2-3.0. In a further example, the ratio is 0.2-1.0 in the presence of the catalyst.

TABLE 1 hydrolysis product yield and distribution
based on GC/MS analysis on liquor product.

|  | Example 1-1 | Example 2-1 | Example 3-1 | Example 4-1 | Example 5-1 |
|---|---|---|---|---|---|
| T (° C.) | 200 | 250 | 200 | 200 | 200 |
| Base/wood (g/g) | 1:2 | 1:2 | 3:1 | 1:3.73 | 1:3.73 |
| Total yield of fuel precursor on the basis of lignin* | 55.1% | 31% | 35.5% | 46.6% | 58% |
| % Phenolics | 9 | 37.2 | 19.2 | 7.8 | 6.0 |
| % Cyclic alcohols | 30.4 | 12.4 | 19.6 | 36.6 | 28.4 |
| % methoxy-benzene | 29.5 | 0 | 22.2 | 29.7 | 22.6 |
| % C1-C4 alcohols | 13.8 | 21.2 | 9.8 | 12.2 | 7.7 |
| % others | 17.3 | 29.2 | 29.2 | 13.7 | 35.3 |

*Assume 17% of the hardwood is the lignin that can be converted to cyclic precursors.

EXAMPLE 5-1

The process described in example 4-1 was repeated except the hydrogen pressure was increase from 500 psig to 1000 psig. The result is also summarized in Table 1. The total yield to products and the yield of cyclohexanols were increased.

EXAMPLE 6-1

A 500 cc Inconel stirred autoclave was charged with 28 g hybrid poplar, 250 g water, 14 g of KOH and 14 g Raney Ni catalyst. The process described in example 5-1 was repeated. The result is shown in Table 2 below.

EXAMPLE 7-1

This example demonstrated the hydrolysis of wood in a larger scale reactor. An 1800 cc stirred autoclave was charged with 112 g of hybrid poplar, 1000 g water, 30 g of KOH and 56 g Raney Ni—Sn catalyst. The reactor was sealed, flushed with nitrogen and pressurized with nitrogen to 100 psig and then hydrogen to total pressure 1100 psig. The reactor was heated to 200° C. and maintained at temperature for 1 hr under stirring. After the mixture was cooled, the residual gas was analyzed. The product mixture was withdrawn, the reactor was rinsed with water and the wash was combined with the product mixture. This product mixture was analyzed using the same procedure described in Example 1-1. The result is shown in Table 2.

EXAMPLE 8-1

This is another example of the hydrolysis of wood in a larger scale reactor. An 1800 cc stirred autoclave was charged with 150 g of hybrid poplar, 1000 g water, 40 g of KOH and 56 g Raney Ni—Sn catalyst. The process described in Example 7-1 was repeated. The result is shown in Table 2.

TABLE 2

Hydrolysis product yield and distribution
based on GC/MS analysis on liquor product

|  | Example 6-1 | Example 7-1 | Example 8-1 |
|---|---|---|---|
| T (° C.) | 200 | 250 | 200 |
| Base/wood (g/g) | 1:3.73 | 1:3.73 | 1:3.73 |
| Total yield of fuel precursor on the basis of lignin* | 76.8% | 79.6% | 77.2% |
| % Phenolics | 9 | 12.4 | 15.3 |
| % Cyclic alcohols | 32.2 | 26.3 | 26.2 |
| % methoxybenzene | 30.4 | 24.5 | 25.4 |
| % C1-C4 alcohols | 12.4 | 8.5 | 11.0 |
| % others | 16.0 | 28.3 | 22.1 |

*Assume 17% of the hardwood is the lignin that can be converted to cyclic precursors.

The following examples disclose additional embodiments of the chemical conversion step 26 (e.g., chain growth) of the method 20.

EXAMPLE 1-2

The following description is representative of the experiments performed. To a 500 cc Inconel stirred autoclave was charged 5 g supported Pd catalyst. The reactor was sealed, flushed with nitrogen followed by pressurization with hydrogen to total pressure 200 psig. The reactor was heated to 325° C. and maintained at temperature for 1 hr to reduce the catalyst before cooling down to room temperature. In further examples, the temperature can be 300-350° C. The residue gas was bled off. The reactor was flushed with $N_2$ and then a mixture of 66 g cyclohexanol and 34 g phenol was introduced into autoclave by syringe. The reactor was then flushed again with nitrogen followed by pressurization with nitrogen to 100 psig and then hydrogen to total pressure 1540 psig. The $H_2$ pressure was determined based on 1.5:1 $H_2$ to cyclohexanol and assumes 3:1 $H_2$ to phenol. The reaction temperature was set at 275° C. and maintained for 16 h under stirring conditions. After the mixture was cooled residual gas was analyzed. The product mixture was withdrawn, the reactor was rinsed with water and the wash was combined with the product mixture. This product mixture was analyzed using the same procedure described in Example 1-1.

EXAMPLE 2-2

The process described in Example 1-2 was repeated except the reaction temperature was increased from 275° C. to 300° C.

EXAMPLE 3-2

The process described in Example 1-2 was repeated except the reaction temperature was increased from 250° C. to 320° C.

TABLE 3

|  | Example 1-2 | Example 2-2 | Example 3-2 |
|---|---|---|---|
| Reaction Temperature (° C.) | 275 | 300 | 320 |
| Catalyst | Pd catalyst | Pd catalyst | Pd catalyst |
| Reactant | Cyclohexanol + phenol | | |
| Yield of C11+ | 68.0 | 57.7 | 62.4 |
| % of 2-cyclohexylcylohexanol | 95.3 | 88.2 | 71.2 |

TABLE 3-continued

|  | Example 1-2 | Example 2-2 | Example 3-2 |
|---|---|---|---|
| % of 1,1'-bicyclohexyl-2-one | 1.7 | 8.4 | 12.7 |
| % of 1,1'-bicyclohexyl | 3 | 1.9 | 12.6 |

EXAMPLE 4-2

The following description is representative of the experiments performed for Examples 4-2 to 6-2. To a 500 cc Inconel stirred autoclave was charged 5 g supported Pd catalyst. The reactor was sealed, flushed with nitrogen followed by pressurization with hydrogen to total pressure 200 psig. The reactor was heated to 325° C. and maintained at temperature for 1 hr before cooling down to room temperature. The residue gas was bled off. The reactor was flushed with $N_2$ and then a mixture of 100 g cyclohexanol was introduced into the autoclave by syringe. The reactor was then flushed again with nitrogen followed by pressurization with nitrogen to 734 psig and then hydrogen to total pressure 2201 psig. The $H_2$ to cyclohexanol was 2:1. The reactor temperature was set at 316° C. and maintained for 16 h under stirring conditions. After the mixture was cooled residual gas was analyzed. The product mixture was withdrawn, the reactor was rinsed with water and the wash was combined with the product mixture. This product mixture was analyzed using the same procedure described in (Example 1-1).

EXAMPLE 5-2

The effect of small amounts of $H_2O$ on the chain growth was studied as follows. The process described in Example 4 was repeated, except the mixture was 100 g cyclohexanol and 3.64 g water. The reactor was pressurized with nitrogen to 300 psig and then hydrogen to a total pressure of 1888 psig. The $H_2$ to cyclohexanol was 2:1. The result is shown in Table 4.

EXAMPLE 6-2

The effect of light alcohols on the chain growth was studied as follows. The process described in Example 4 was repeated, except the mixture was 61 g cyclohexanol, 26 g phenol, 13 g ethanol and 3 g water. The reactor was pressurized with nitrogen to 181 psig and then hydrogen to a total pressure of 1695 psig. The $H_2$ pressure was determined base on 2:1 $H_2$ to cyclohexanol and with 3:1 $H_2$ to phenol. The result is shown in Table 4.

EXAMPLE 7-2

Example 6-2 was repeated using a mixed oxide supported Co catalyst instead of a supported Pd catalyst. The result is shown in Table 4.

TABLE 4

|  | Example 4-2 | Example 5-2 | Example 6-2 | Example 7-2 |
|---|---|---|---|---|
| Temperature (° C.) | 316 | 316 | 316 |  |
| Catalyst | Pd catalyst | Pd catalyst | Pd catalyst | Co catalyst |
| Reactant | Cyclo- | Cyclo- | Cyclohexanol + phenol + | |

TABLE 4-continued

|  | Example 4-2 | Example 5-2 | Example 6-2 | Example 7-2 |
|---|---|---|---|---|
|  | hexanol | hexanol + H2O | ethanol + H2O | |
| Yield of C11+ | 64.3% | 45.4% | 0.65% | 12.3% |
| % of 2-cyclohexyl-cylohexanol | 97.4 | 98.4 | 100 | 70.8 |
| % of 1,1'-bicyclohexyl-2-one | 2.6 | 1.6 | 0 | 6.4 |
| % of 1,1'-bicyclohexyl | 0 | 0 | 0 | 12.2 |

EXAMPLE 8-2

The ether extract from (Example 8-1) was rotary evaporated to obtain targeted chemical fragments without ether. The process of (Example 8-1) was repeated in order to obtain enough quantity of targeted chemical fragments to be further processed. A total of 12 g of targeted chemical fragments were dissolved in hexane to a total volume of 80 mL. The process described in (Example 1-2) was repeated except the $H_2$ pressure was 640 psig and the $N_2$ pressure was 860 psig and increased to a total pressure of 1500 psig. The total yield of C9-C12 hydrocarbons was 30%.

The following examples disclose additional embodiments of the second decomposition step 24 (e.g., extraction) of the method 20.

EXAMPLE 1-3

A liquor from step 22 was extracted by $CO_2$ supercritical extraction to remove water. The extractions were performed at 200 bar and 50° C., with a $CO_2$ solvent to feed ratio of 20. The results are given in Table 5.

TABLE 5

| Supercritical $CO_2$ extraction of biomass hydrolysis sample, 200 bar, 50° C. | | | |
|---|---|---|---|
|  | Mass of precursors sample (mg) | | |
|  | Pre Extraction | Post Extraction | Extraction Efficiency (%) |
| Biomass Hydrolysis Sample | 165 | 28 | 83.0% |

EXAMPLE 2-3

A mixture of typical model compounds found in liquors from the wood hydrolysis was extracted by $CO_2$ supercritical extraction to remove water. The extractions were performed at 200 bar and 50° C., with a solvent to feed ratio of 20. The results are given in Table 6.

TABLE 6

Supercritical CO₂ extraction of a model
compound mixture, 200 bar, 50° C.

| Compound | Mass in sample (mg) | | Extraction Efficiency (%) |
|---|---|---|---|
| | Pre Extraction | Post Extraction | |
| ethanol | 40.3 | 22.6 | 44.0 |
| Cyclohexanol | 130.1 | 11.8 | 90.9 |
| Acetic Acid | 110.1 | 114.2 | −3.8 |
| 2-methoxy-phenol | 58.4 | 7.0 | 88.1 |
| 1,2,3 Trimethoxy benzene | 38.2 | 5.3 | 86.2 |
| Phenol | 58.3 | 25.0 | 57.2 |
| 1,2,4 Trimethoxy benzene | 34.3 | 5.4 | 84.4 |
| Eugenol | 15.7 | 0.3 | 97.9 |

Figure 2:
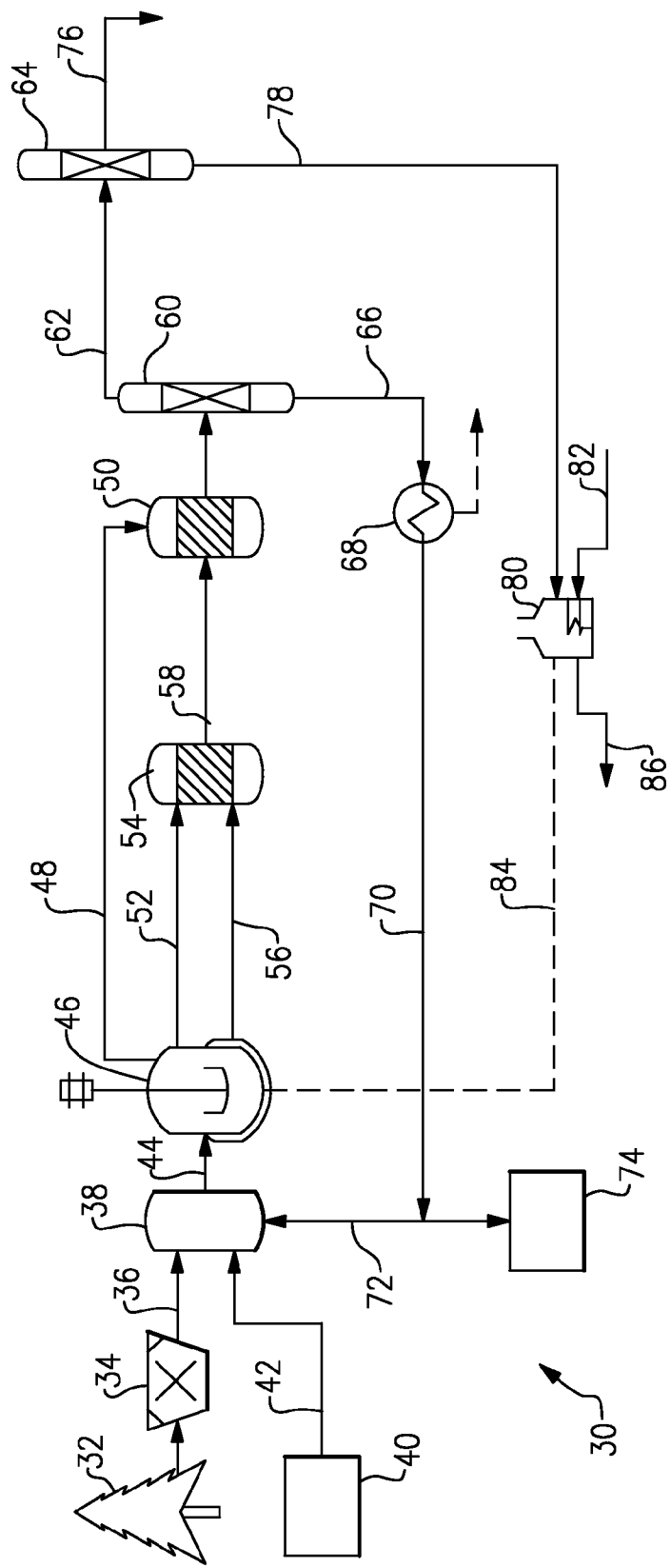
FIG. 2 illustrates an example processing system for processing a biomass material to produce a biofuel.

FIG. 2 illustrates an example processing system 30 for implementing one embodiment of the method 20. In this example, the processing system 30 includes lignocellulosic material 32. The lignocellulosic material 32 is pulverized in grinder 34 and fed through line 36 into a wet slurry tank 38. A solution storage tank 40 feeds caustic solution through line 42 into the wet slurry tank 38. The resultant slurry is fed through line 44 into a reactor 46 in which the first decomposition step 22 and, optionally, the second decomposition step 24 are carried out. In an example, step 22 is conducted at a temperature of 300-330° C. with a ratio of base to wood (weight of base divided by weight of wood, g/g) of 0.2-1.0. In a further example, the ratio is 0.5-1.0. Byproduct hydrogen-rich gas from the first decomposition step 22 or second decomposition step 24 is fed through line 48 into an optional hydrotreater 50. The hydrogen gas is also fed through line 52 into a chain growth reactor 54.

The fragments from the decomposition of the lignin are fed through line 56 from the reactor 46 into the chain growth reactor 54. The chemical conversion step 26 is carried out in the chain growth reactor 54. The effluent stream from the chain growth reactor 54 is fed through line 58 into the optional hydrotreater 50. If the hydrotreater 50 is not used the effluent stream may be fed directly into a separator 60, which separates a stream that contains the biofuel from a waste stream. The biofuel-containing stream is fed through line 62 to an optional fractionation device 64 to further process and separate the biofuel.

The waste stream is fed through line 66 to a waste recovery system 68, which is used to capture waste heat and energy from the waste stream. The water or other waste materials that are not recovered in the waste recovery system 68 are fed through line 70 into a purge line 72 that either feeds the waste materials back into the wet slurry tank 38 or into a purge 74.

The biofuel is fed from the fractionation device 64 through line 76 for downstream use, such as the electricity production. A waste stream is fed through line 78 to an optional burner 80. The burner 80 receives the waste stream and an airstream 82 to produce a heat output 84 that is fed into the reactor 46. An exhaust stream 86 is purged.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A method for processing biomass to produce biofuel, the method comprising:
   decomposing lignocellulosic material into byproduct polymers that include lignin;
   decomposing the lignin into targeted chemical fragments that include oxygenates; and
   chemically converting the targeted chemical fragments by reacting the targeted chemical fragments with each other to produce biofuel hydrocarbons having from 9 to 16 carbon atoms.

2. The method as recited in claim 1, including decomposing the lignocellulosic material in a slurry having a pH of 8 or greater at a temperature between 180° C. and 250° C.

3. The method as recited in claim 2, wherein the slurry is an aqueous slurry that comprises an alkaline component.

4. The method as recited in claim 2, including decomposing the lignocellulosic material in the presence of a heterogeneous catalyst and at a pressure that is greater than 5 atmospheres.

5. The method as recited in claim 1, including separating the lignin from the byproduct polymers.

6. The method as recited in claim 5, including catalytically reforming the byproduct polymers which are substantially free of the lignin, to produce hydrogen.

7. The method as recited in claim 6, including using the hydrogen from the catalytic reforming in the decomposing of the lignocellulosic material.

8. The method as recited in claim 6, including using the hydrogen from the catalytic reforming in the decomposition of lignin into the targeted chemical fragments.

9. The method as recited in claim 5, wherein the byproduct polymers include cellulose, and including decomposing the cellulose to a hydrocarbon material having six carbon atoms using a catalyst material that includes at least one of cobalt, nickel, tin, platinum, rhenium, palladium and combinations thereof.

10. The method as recited in claim 1, including catalytically converting the targeted chemical fragments of the lignin to produce the hydrocarbons having from 9 to 16 carbon atoms using a catalyst material that includes at least one of cobalt, nickel, tin, platinum, rhenium and palladium or combinations thereof.

11. The method as recited in claim 1, wherein the targeted chemical fragments of the lignin include 9 or less carbon atoms.

12. A method for processing biomass, the method comprising:
   decomposing lignocellulosic material into byproduct polymers that include lignin;
   decomposing the lignin into short-chain hydrocarbon fragments having 9 carbon atoms or less; and
   chemically converting the short-chain hydrocarbon fragments into a biofuel that includes hydrocarbons having from 9 to 16 carbon atoms by reacting the short-chain hydrocarbon fragments with each other.

13. The method as recited in claim 12, including separating the lignin from the byproduct polymers.

14. The method as recited in claim 13, including catalytically reforming the byproduct polymers which are substantially free of the lignin, to produce hydrogen, and using the hydrogen from the catalytic reforming in the decomposing of the lignocellulosic material.

15. The method as recited in claim 1, wherein the oxygenates include at least one of simple alcohols, cyclic alcohols, and methoxy benzenes, and mixtures thereof.

16. The method as recited in claim 1, wherein the oxygenates include cyclic alcohols.

17. The method as recited in claim 1, wherein the oxygenates include at least one of cyclopentanols, cyclohexanols, alkylcyclopentanols, alkylcyclohexanols, phenols, alkylphenols, or mixtures thereof.

18. A method for processing biomass to produce biofuel, the method comprising:
- decomposing lignocellulosic material into byproduct polymers that include lignin;
- decomposing the lignin into targeted chemical fragments; and
- chemically converting the targeted chemical fragments to produce a biofuel.

* * * * *